United States Patent [19]
Waters

[11] Patent Number: 5,979,067
[45] Date of Patent: Nov. 9, 1999

[54] DEVICE AND RELATED METHOD FOR MEASURING FOOT POSTURE

[76] Inventor: Greg Waters, 2345 Pfister Hwy., Adrian, Mich. 49221

[21] Appl. No.: 08/850,087

[22] Filed: May 2, 1997

[51] Int. Cl.$^6$ .................................................. A61B 5/103
[52] U.S. Cl. .............................. 33/512; 33/515; 600/595; 600/592
[58] Field of Search .............................. 33/515, 511, 512, 33/534, 114, 549; 600/592, 595, 587

[56] References Cited

U.S. PATENT DOCUMENTS

| | | | |
|---|---|---|---|
| 2,043,187 | 6/1936 | Owens | 600/592 |
| 3,826,145 | 7/1974 | McFarland | 600/595 |
| 4,305,571 | 12/1981 | McLeod | 254/291 |
| 4,398,429 | 8/1983 | Cook | 73/862.045 |
| 4,883,069 | 11/1989 | McLeod | 600/595 |
| 5,038,489 | 8/1991 | Muehlenbein | 33/512 |
| 5,080,109 | 1/1992 | Arme, Jr. | 33/515 |
| 5,168,634 | 12/1992 | Misevich | 33/515 |
| 5,435,320 | 7/1995 | Seitz | 600/595 |

FOREIGN PATENT DOCUMENTS 2405059  6/1979  France ...................... 33/515

*Primary Examiner*—Christopher W. Fulton
*Attorney, Agent, or Firm*—Brinks Hofer Gilson & Lione

[57] ABSTRACT

The present invention provides a method and device for evaluating foot posture and its effect of the functional biomechanics of the lower extremities. The device is divided into one half and another half, both of which are identical mirror images and which are connected by a releasable connecting member. Each section includes a split-surface platform mounted on a frame. The split-surface platform has a front and a rear plate. The front and rear plates each have a means for adjusting the horizontal angle of the plate through a range of 25° in either direction and a means for indicating the specific angle. The mechanics of the front and rear plates are not connected to each other, thus allowing independent manipulation of the front and rear portion of the patient's foot. The rear plate may be fitted with variable height booster plates for providing sagittal plane control for limb length discrepancies as well as for accommodating high-arched (equinas) foot types. A non-slip surface may be applied to the upper surface of the front and rear plates, as well as the booster plates, to help prevent the patient's foot from slipping from the plate surfaces.

18 Claims, 4 Drawing Sheets

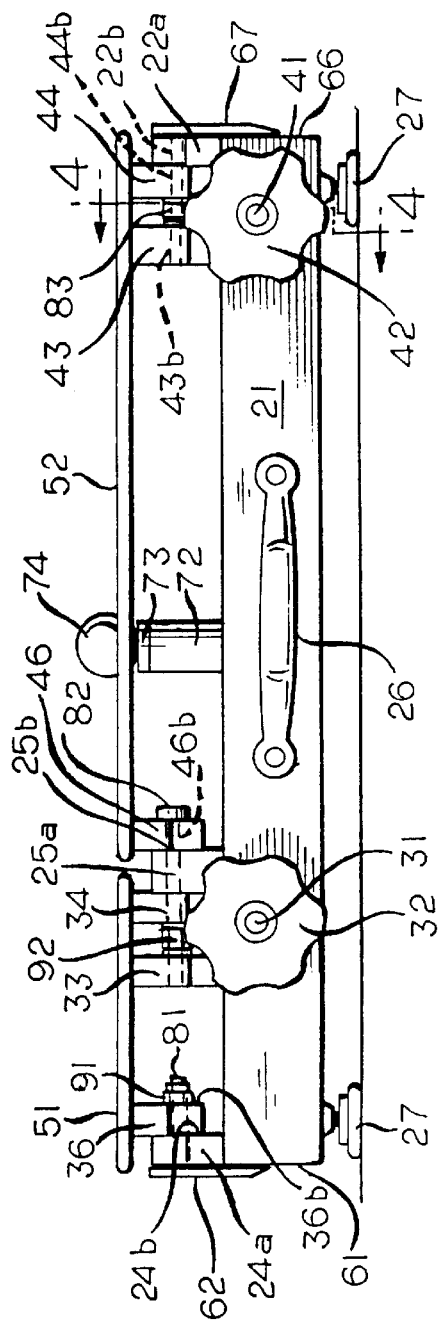
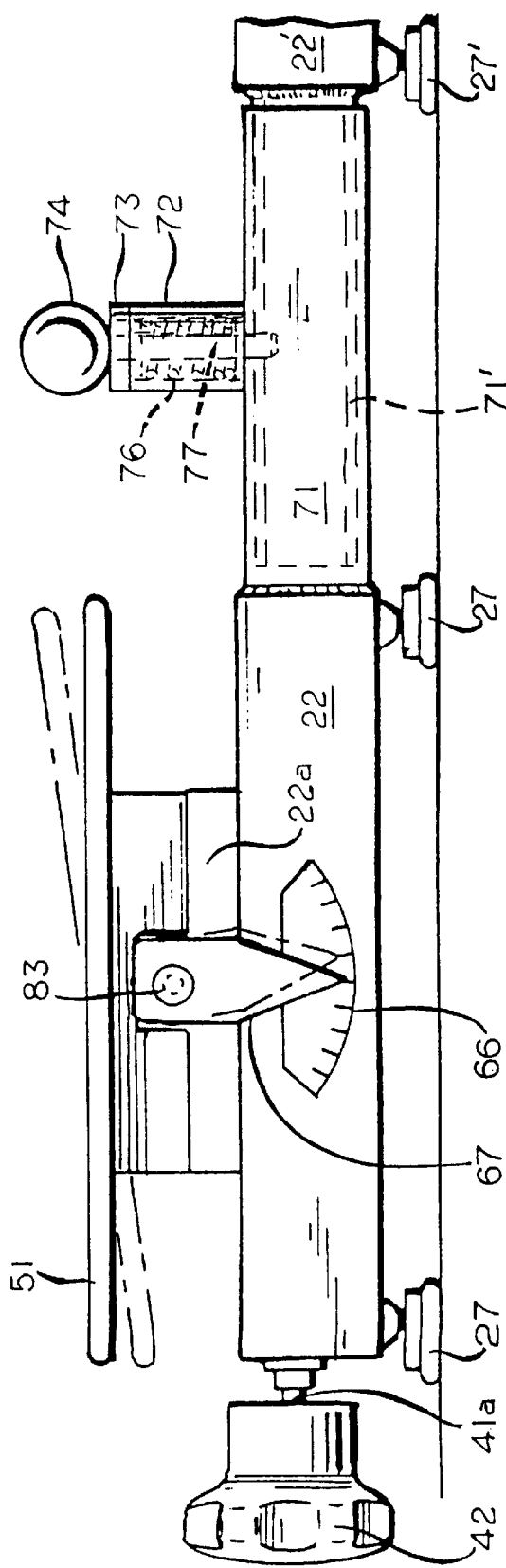
FIG. 3
FIG. 5

DEVICE AND RELATED METHOD FOR MEASURING FOOT POSTURE

FIELD OF THE INVENTION

The present invention relates to a method and device in the field of physical therapy; more specifically, the present invention relates to a method and device for evaluating foot posture and its effect on the functional biomechanics of the lower extremities, including the knee and hip joints.

BACKGROUND

During evaluation of a patient's foot, a physical therapy practitioner requires a means for dynamic measurement with respect to a subtalor neutral position, or optimal position, for foot function. The subtalor neutral position is characterized by the congruency of the head of the talus. During pronation, the talus will adduct and plantarflex; therefore the talar head can be palpated medially. Conversely, during supination the talus will abduct and dorsiflex, thus becoming more prominent laterally. To determine the subtalor neutral position of a patient's foot, the thumb and finger of the therapist is placed on the foot and the joint is alternately supinated and pronated until a position is found where the medial and lateral sides of the talus are neither protruding nor depressed between the finger/thumb placement. It is at this point that the congruency of the subtalor joint (with resulting neutrality) has been achieved.

Once a precise evaluation of the foot is obtained, the physical therapist can then recommend treatment to correct the flaws in the foot and restore ideal static and dynamic function to the foot. One such treatment is the use of an orthotic device, a custom made shoe insert designed specifically for the individual foot of the patient. Using the evaluation of the foot, the orthotic is constructed to mechanically force the foot into the subtalor neutral position for optimal foot performance. Of course, an accurate evaluation of the patient's foot is critical to the success of any orthotic.

Numerous devices have been developed over the years that examine the force distribution of the foot in both the static and dynamic environments. Although these evaluation tools have the ability to show forced production of a pathological foot, they do not provide specific objective measures of the foot that would provide the evaluator strategy for immediately restoring the ideal mechanics of the foot and to observe the immediate effects of the corrected posture.

The forgoing discussion suggests not only the desirability of a device and method for measuring the posture of a patient's foot, but also suggests the various applications for which such a device and method may be used. Accordingly, the present invention provides a solution to the problems mentioned above.

SUMMARY

The present invention provides a method and device for evaluating foot posture and its effect of the functional biomechanics of the lower extremities. The device is divided into two halves, which are identical (but are a mirror image of the other) and which are connected by a releasable connecting member. Each section includes a split-surface platform mounted on a frame. The split-surface platform has a front and a rear plate. The front and rear plates each have a means for adjusting the horizontal angle of the plate through a range of 25° in the clockwise (varus) direction to 25° in the counterclockwise (valgus) direction and a means for indicating the specific angle in degrees. The mechanics of the front and rear plates are not functionally connected to each other, thus allowing independent manipulation of the front and rear portion of the patient's foot. The rear plate may be fitted with variable height booster plates for providing sagittal plane control for limb length discrepancies as well as for accommodating high-arched (equinas) foot types.

By providing the therapist with an accurate evaluation of the patient's feet, several advantages can be realized. Using orthotics or other corrective measures, the patient's balance and overall posture can be improved. The patient may also enjoy improved function through the corrected bony relationship of lower extremities, i.e., ankles, knees, hips, etc. In addition, use of the present invention is not limited to diagnosing the flaws in a patient's feet. It may be also used to: improve the performance of an athlete (such as a runner or a golfer); design high tech shoes, ski boots, or skates; evaluate a patient after surgery; or, limit the range of a patient's knee or ankle during physical rehabilitation.

Accordingly, it is an object of the present invention to provide a device and method for accurately measuring the posture of a patient's foot.

It is a further object of the present invention to provide a device and method for training athletes in the area of joint awareness and movement.

It is a still further object of the present invention to provide a device and method for aiding in the design of sports shoes, ski boots, skates, and the like.

Still further objects and advantages of the present invention will become apparent by reference to the following description of the preferred and alternate embodiments and appended drawings.

BRIEF DESCRIPTIONS OF THE DRAWINGS

FIG. 3 shows an elevational side view of the invention shown in FIG. 1.

FIG. 5 shows a front elevational view of the invention show in FIG. 1.

DETAILED DESPCRIPTION OF THE PREFERRED EMBODIMENT

System Overview

Figure 1:
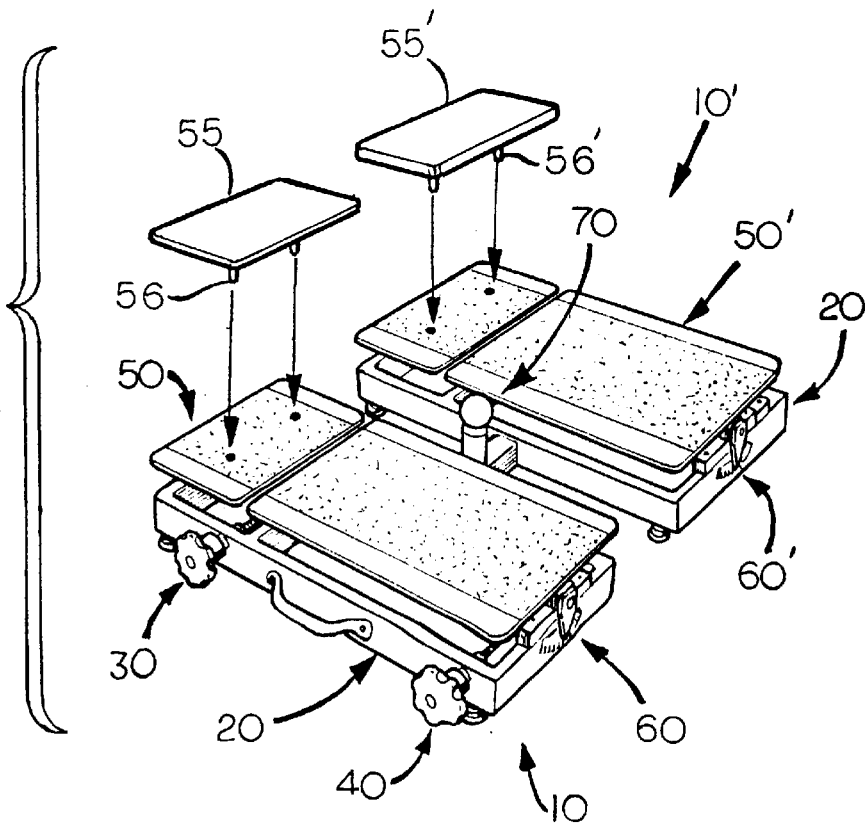
FIG. 1 shows a perspective view of the preferred embodiment of the present invention.

Referring now to FIGS. 1–6, the present invention provides a method and device for the measurement of the posture of a foot, the device of which is divided into two halves generally referred to as reference numerals 10 and 10'. The construction of one half of the present invention 10 is identical to the that of the other half 10' except for the connection assembly 70 which is constructed as shown in FIGS. 1–5. In general, one half the invention 10 includes a frame 20, a rear adjustment mechanism 30, a front adjustment mechanism 40, a split-surface platform 50, an angle indicating means 60, and a connection assembly 70. The mirror image components of the other half of the invention 10' are referred to by the reference numerals of the one half 10 with an added "'"; for example, as shown in FIG. 1, 50 refers to the foot plate assembly of one half of the invention 10 while 50' refers to the foot plate assembly of the other half 10'.

Frame

The frame 20 of the present invention includes frame members 21–24, a support member 25, a carrying handle 26, and frame supports 27. In the preferred embodiment, the frame members 21–24 are attached together using bolts, welding, or the like in a rectangular arrangement with the support member 25 attached perpendicular to frame members 21 and 23 and parallel to frame members 22 and 24, partially shown in FIG. 2. The frame members 21–24 and the support member 25 are typically made of metal bar stock, but can be made from any rigid material with the requisite structural and load bearing capabilities. The frame supports 27 are off-the-shelf items which include a threaded rod (not shown) which screws into the underside of frame members 21 and 23. The threaded rod connection (not shown) to the frame members 21 and 23 allows the height of each individual frame support 27 to be adjusted to accommodate any uneven surface upon which the device 10 may be resting. Finally, to facilitate transporting the device 10, the carrying handle 26 is mounted to the side of the frame member 21 using bolts, welding, or the like.

Also included in the frame 20 is a rear frame block 24a, a middle frame block 25a, and a front frame block 22a. Each identical frame block 24a, 25a, and 22a is made of aluminum or similar material which is formed in the shape of an inverted "T" best shown in FIGS. 2 and 3. The rear frame block 24a is attached to the upper surface of the frame member 24 using bolted, welded, or similar means such that the frame member 24 and the rear frame block 24a are longitudinally aligned. Middle frame block 25a and front frame block 22a are attached to the support member 25 and the frame member 22, respectively, in a like manner. Each frame block 22a, 25a, and 22a has a passage 22b, 25b, and 22b formed therein as shown in FIG. 3, the function of which will be discussed later herein.

Rear Adjustment Mechanism

Figure 6:
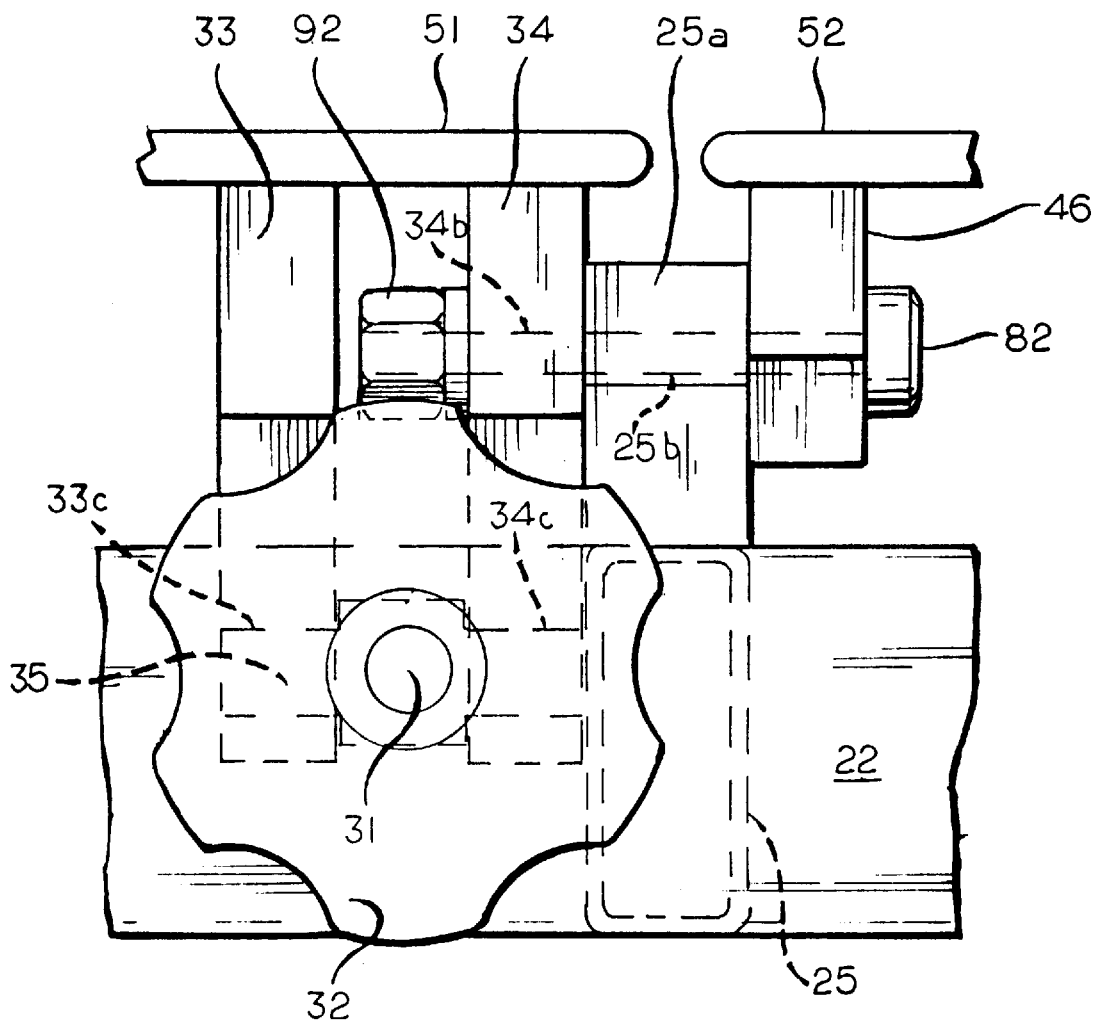
FIG. 6 shows an enlarged partial elevational side view of the invention shown in FIG. 3.

Referring now primarily to FIGS. 3 and 6, the rear adjustment mechanism 30 includes a rear adjustment rod 31, a rear adjustment knob 32, three rear adjustment blocks 33, 34, and 36, and a rear adjustment connector 35. The rear adjustment blocks 33, 34, and 36 are constructed of aluminum or a like material and is formed into an upright T-shaped configuration, similar or identical to the aforementioned frame blocks 22a, 25a, and 22a, but inverted in orientation. The rear adjustment block 33 has a passage 33c formed therein; the rear adjustment block 34 has passages 34b and 34c; and, the rear adjustment block 36 has a passage 36b, , shown in FIGS. 3 and 6.

The rear adjustment block 36 is pivotally connected to the rear frame block 24a by a thru-bolt 81 (which passes through passages 36b and 24b, respectively) and is secured by retaining nut 91. Similarly, the rear adjustment block 34 is pivotally connected to the middle frame block 25a by a thru-bolt 82 (which passes though the passages 34b and 25b, best shown in FIG. 6) and is secured by retaining nut 92.

The rear adjustment block 33 is connected to the rear adjustment block 34 via the rear adjustment connector 35. The rear adjustment connector is cylindrical in shape and is positioned between the rear adjustment blocks 33 and 34 utilizing passages 33c and 34c. The rear adjustment connector 35 has a threaded passage (not shown) in its center transverse to the longitudinal axis of the rear adjustment connector 35.

The rear adjustment mechanism 30 is completed by the rear adjustment knob 32 which is connected to the rear adjustment rod 31 which passes through a hole in the frame member 21. The rear adjustment rod 31 has threads which engage the aforementioned threaded passage (not shown) in the rear adjustment connector 35. In the preferred embodiment, a spacer or bushing 31a is placed between the inside edge of the rear adjustment knob 32 and the outside edge of the frame member 21 to prevent friction. Finally, a set screw (not shown) is located within the rear adjustment block 36 is used to calibrate the angle of the rear plate 51 to 0° with respect to a horizontal plane.

Front Adjustment Mechanism

Figure 4:
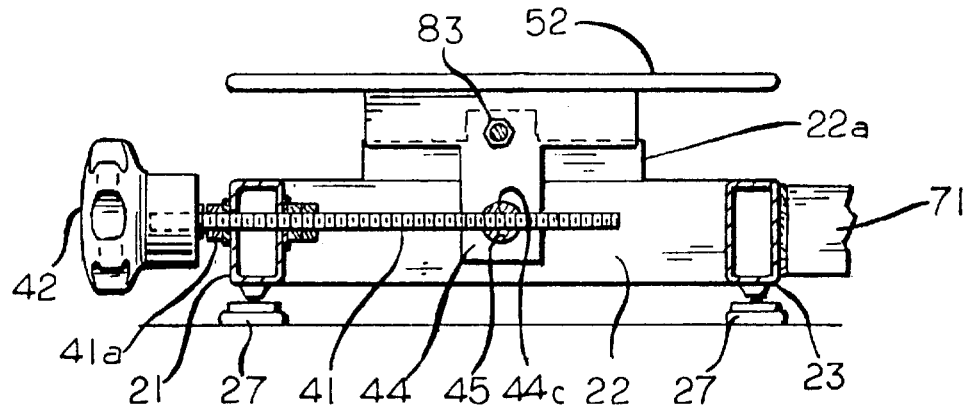
FIG. 4 shows a sectional view along line 4—4 of the invention shown in FIG. 3.

The front adjustment mechanism 40, best shown in FIGS. 3 and 4, is nearly identical to the aforementioned rear adjustment mechanism 30. The front adjustment mechanism includes a front adjustment rod 41, a front adjustment knob 42, three front adjustment blocks 43, 44, and 46, and a front adjustment connector 45. The front adjustment blocks 43, 44, and 46 are very similar to rear adjustment blocks 33, 34, and 36. The front adjustment block 43 has a passage 43b formed therein; the front adjustment block 44 has passages 44b and 44c; and, the front adjustment block 46 has a passage 46b, , shown in FIGS. 3 and 6.

The front adjustment block 46 is pivotally connected to support member block 25a by a thru-bolt 82 (which passes through passages 46b and 25b, respectively) and is secured by retaining nut 92, best shown in FIG. 6. Similarly, the front adjustment blocks 43 and 44 are pivotally connected to the front frame block 22a by a thru-bolt 83 (which passes though the passages 43b, 44b and 22b, best shown in FIG. 3).

The front adjustment block 43 is connected to the front adjustment block 44 via the front adjustment connector 45 in an arrangement identical to the rear adjustment mechanism. The front adjustment connector 45 is cylindrical in shape and is positioned between the front adjustment blocks 43 and 44 utilizing the passages in each, not shown and 44c, respectively. Like the rear adjustment connector 35, the front adjustment connector 45 also has a threaded passage (not shown) in its center transverse to the longitudinal axis of the front adjustment connector 45.

The front adjustment mechanism 40 is completed by the front adjustment knob 42 which is connected to the front adjustment rod 41 which passes through a hole in the frame member 21. The front adjustment rod 41 has threads which engage the aforementioned threaded passage (not shown) in the front adjustment connector 45. In the preferred embodiment, a spacer or bushing 41a is placed between the inside edge of the front adjustment knob 42 and the outside edge of the frame member 21 to prevent friction. Like the rear adjustment mechanism 30, the front adjustment mechanism 40 also includes a set screw (not shown) located in front adjustment block 44 to calibrate the angle of the front plate 52.

Split-Surface Platform

The split-surface platform 50 includes a rear plate 51, a front plate 52, an anti-slip material 53, and alignment holes 54, and may include one or more booster plates 55, best shown in FIG. 1.

The rear plate 51 is attached to rear adjustment blocks 36, 33, and/or 34 using bolts, welding, or the like. The rear plate 51 is constructed of a plate of high strength metal, but any rigid material which similar properties may be used. The anti-slip material 53 is applied to the upper surface of the rear plate 51 with an adhesive to aid in preventing a patient's foot from sliding. Finally, the booster plate 55 may be added to the rear plate 51 by placing the booster plate 55 on the upper surface of the rear plate 51 and inserting alignment pegs 56 into alignment holes 54 to compensate for a foot having a very high arch. A number of interchangeable booster plates 55, which are made from a plate of metal similar to that of the rear plate 51 or the like, are made in varying thicknesses to allow for differences in the arches of various patients.

The front plate 52 is similar to the rear plate 51 in construction, but has a greater surface area to accommodate the forward portion of a patient's foot. The front plate 52 is attached to the middle frame block 25a, the front adjustment block 46, and the front adjustment blocks 43 and 44 using bolts, welding, or the like. A similar material to that used in constructing rear plate 51 is used to construct front plate 52. An anti-slip material is also applied to the upper surface of front plate 52.

Angle Indicating Means

The angle indicating means 60 includes a rear angle label 61, a rear angle pointer 62, a front angle label 66 and a front angle pointer 67. The angle labels 61 and 66 are flat labels made in an arcuate shape (shown best in FIG. 5) and are constructed of paper, plastic, or a like material having angle increments embossed or printed on the outer surface. The rear angle label 61 is affixed to the outer surface of the frame member 24 using an adhesive; the front angle label 66 is affixed to the outer surface of the frame member 22 in a like manner. Each of the angle pointers 62 and 67 is a relatively flat component having a lower pointed end which is capable of "sweeping" across the face of the angle labels 61 and 66. The angle pointers 62 and 67 are constructed of any appropriate rigid material. The angle pointer 62 is secured affixed to the thru-bolt 81 such that any rotation of the thru-bolt 81 results in corresponding rotational movement of the angle pointer 62. The angle pointer 62 is mounted nearly flush with the outer edge of the frame member 24, as shown in FIG. 3. Similarly, the angle pointer 67 is securely affixed to thru-bolt 83 such that any rotation of the thru-bolt 83 results in corresponding rotational movement of the angle pointer 67. The angle pointer 67 is mounted nearly flush with the frame member 22, also shown in FIG. 3.

Connection Assembly

The connection assembly 70 is a simple mechanism and is not critical to the function of the present invention; the connection assembly 70 need only connect the one half of the invention 10 to the other half 10' in a sturdy manner and be relatively easy to operate for repeated connections/disconnections. The connection assembly 70 includes connection members 71 and 71', connection cylinder 72, cylinder cap 73, release knob 74, cylinder spring 76, and connection rod 76. The connection members 71 and 71' are connected to the frame members 22 and 22', respectively, by welding, bolts, or the like, and are made of square tubing or equivalent. The outside dimensions of the connection member 71' are slightly smaller than the inside dimensions of the connection member 70 (or vice versa) so that the connection members 71 and 71' can slidably engage, as shown in FIG. 5. The connection cylinder 72 is mounted to the upper surface of connection member 71 and is threaded inside. The connection rod 77 is also threaded and engages the threads of the connection cylinder 72. The release knob 74 is fixed to the top of the connection rod 77 and the cylinder spring 76 is located so that the release knob 74 and the connection rod 77 are "spring loaded." The connection rod 77 extends beyond the bottom edge of the connection cylinder 72 and engages a connection hole (not shown) located in the upper surface of the connection member 71'.

Operation

Figure 2:
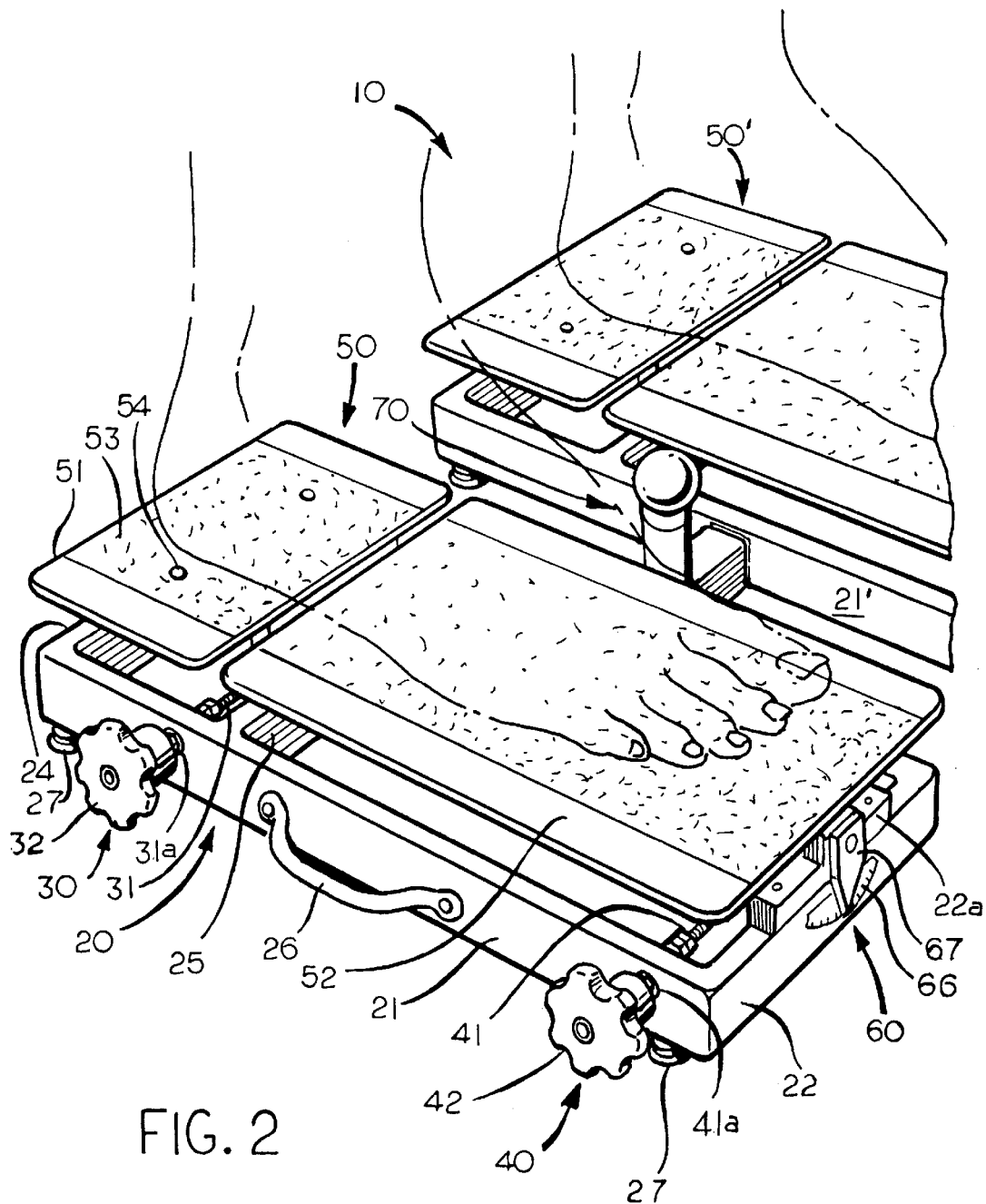
FIG. 2 shows an enlarged perspective partial view of the invention shown in FIG. 1.

The operation of the one half 10 of the present invention is as follows. A patient's foot is placed on the split-surface platform 50 such that the heel of the foot is resting on the rear plate 51 and the forward portion of the foot is resting on the front plate 51 as shown in FIG. 2. Any booster plate 55 necessary to compensate for the structure of the foot is added by inserting the alignment pegs 56 of the appropriate booster plate 55 into the alignment holes 54 of the rear plate 51. The user, for example, a physical therapist, then adjusts the horizontal angle of the rear plate 51 by turning the rear adjustment knob 32. As the user turns the rear adjustment knob 32 in either direction, the rear adjustment rod 31 engages the threads of the rear adjustment connector 35 and causes the rear plate 51 to pivot about thru-bolts 81 and 82. The rear angle pointer 62 is attached to the thru-bolt 81 such that one degree of horizontal tilt to the rear plate 51 causes the angle pointer 61 to point to the "one degree" mark on the face of the angle label 62. The user ceases to adjust the horizontal angle of the rear plate 51 when the foot reaches the subtalor neutral position, that is, the position which allows the foot to achieve optimum performance. The subtalor neutral position of a foot is characterized by the congruency of the head of the talus as previously described herein. The angle of elevation in either the inverted or everted direction is then obtained by observing the position of the rear angle pointer 67 on the rear angle label 66.

The process is then repeated for the forward portion of the foot, if necessary (depending upon the individual foot structure, use of the rear adjustment mechanism 30 may be enough to place the foot into the subtalor neutral position; in other cases, use of the front adjustment mechanism 40 is necessary to manipulate the foot into the correct posture). The user adjusts the horizontal angle of the front plate 52 by turning the front adjustment knob 42. As the user turns the front adjustment knob 42 in either direction, the front adjustment rod 41 engages the threads of the front adjustment connector 45 and causes the front plate 52 to pivot about thru-bolts 82 and 83. The front angle pointer 67 is attached to the thru-bolt 83 such that one degree of horizontal tilt to the front plate 52 causes the angle pointer 67 to point to the "one degree" mark on the face of the angle label 66. The user ceases to adjust the horizontal angle of the front plate 52 when the foot reaches the subtalor neutral position and again the angle of elevation in either the inverted or everted direction is obtained by observing the position of the front angle pointer 67 on the front angle label 66.

Although the best mode contemplated by the inventors for carrying out the present invention as of the filing date hereof has been shown and described herein, it will be apparent to those skilled in the art that suitable modifications, variations, and equivalents may be made without departing from the scope of the invention, such scope being limited solely by the terms of the following claims.

What is claimed is:

1. A measuring device comprising:
   a frame;
   a platform being mounted on said frame, said platform having a front section and a rear section;
   means for adjusting the angle of said front section of said platform;
   means for indicating said angle of said front section of said platform;
   means for adjusting the angle of said rear section of said platform comprising:
   a rear pivot bolt being pivotally attached to said plurality of rear platform supports;
   a rear platform support connector connecting said plurality of rear platform supports;
   a rear adjustment rod, said rear adjustment rod being connected to said rear platform support connector;

and a knob connected to said rear adjustment rod such that rotation of said knob causes said rear section of said platform to pivot about said front pivot bolt, means for indicating said angle of said rear section of said platform, and a plurality of rear adjustment supports being attached to the underside of said rear section and said front section of said platform and further being attached to said frame.

2. The device according to claim 1 wherein said frame comprises four frame members connected together in a rectangular configuration.

3. The device according to claim 1 wherein said frame further comprises at least one support member connected to said frame members.

4. The device according to claim 1 further comprising means for calibrating said rear section whereby the angle of said rear section is 0° with respect to a horizontal plane.

5. The device according to claim 4 wherein said means for calibrating said rear section comprises a set screw located in one of said plurality of rear adjustment supports.

6. The device according to claim 1 wherein said means for indicating said angle of said rear section comprises:

a rear angle pointer being connected to said rear pivot bolt, said rear angle pointer capable of moving in increments corresponding to the movement of said rear plate; and, a rear angle label being attached to said frame and having markings thereon for indicating said angle of said rear plate.

7. The device according to claim 6 wherein said markings indicate said angle of said rear plate in degrees.

8. A measuring device comprising:

a frame;

a platform being mounted on said frame, said platform having a front section and a rear section;

means for adjusting the angle of said front section of said platform;

means for indicating said angle of said front section of said platform comprising;
  a front pivot bolt being pivotally attached to said plurality of front platform supports;
  a front platform support connector connecting said plurality of front platform supports;
  a front adjustment rod being connected to said front platform support connector, and a knob connected to said front adjustment rod such that rotation of said knob causes said front section of said platform to pivot about said front pivot bolt, means for adjusting the angle of said rear section of said platform, means for indicating said angle of said rear section of said platform, and a plurality of front adjustment supports being attached to the underside of said front section and said front section of said platform and further being attached to said frame.

9. The device according to claim 8 further comprising means for calibrating said front section whereby the angle of said front section is 0° with respect to a horizontal plane.

10. The device according to claim 9 wherein said means for calibrating said front section comprises a set screw located in one of said plurality of front adjustment supports.

11. The device according to claim 8 wherein said means for indicating said angle of said rear section comprises:

a rear angle pointer being connected to said rear pivot bolt, said rear angle pointer capable of moving in increments corresponding to the movement of said rear plate; and, a rear angle label being attached to said frame and having markings thereon for indicating said angle of said rear plate.

12. The device according to claim 11 wherein said markings indicate said angle of said rear plate in degrees.

13. A device for measuring the posture of a foot, said device comprising:

a frame having a front section and a rear section;

a rear plate being mounted to said rear section of said frame;

at least two rear adjustment blocks being attached to an upper surface of said rear section of said frame and further attached to the underside of said rear plate;

a rear thru-bolt pivotally connecting said at least two rear adjustment blocks to said rear section of said frame;

a rear adjustment connector connecting said at least two rear adjustment blocks, said rear adjustment connector having a threaded passage therethrough;

a rear adjustment rod having a threaded end, said rear adjustment rod passing through a hole in said rear section of said frame and being connected to said rear adjustment connector, said threaded end of said rear adjustment rod engaging said threaded passage in said rear adjustment connector; and, a rear adjustment knob being fixed to said rear adjustment rod;

a front plate being mounted to said front section of said frame;

at least two front adjustment blocks being attached to an upper surface of said front section of said support frame and further attached to the underside of said front plate;

a front thru-bolt pivotally connecting said at least two front adjustment blocks to said front section of said frame;

a front adjustment connector connecting said at least two front adjustment blocks, said front adjustment connector having a threaded passage therethrough;

a front adjustment rod having a threaded end, said front adjustment rod passing through a hole in said front section of said frame and being connected to said front adjustment connector, said threaded end of said front adjustment rod engaging said threaded passage in said front adjustment connector; and, a front adjustment knob being fixed to said front adjustment rod.

14. The device according to claim 13 wherein said means for indicating said angle of said rear plate comprise:

a rear angle pointer being connected to said rear thru-bolt, at least a portion of said rear angle pointer extending alongside said rear section of said frame; and, a rear angle label being affixed to an outside surface of said rear section of said frame, said rear angle label comprising a relatively flat sheet of material having markings for indicating said angle of said rear plate.

15. The device according to claim 14 wherein said markings indicate said angle of said rear plate in degrees.

16. The device according to claim 13 wherein said means for adjusting the angle of said front plate comprises:

at least two front adjustment blocks being attached to an upper surface of said front section of said support frame and further attached to the underside of said front plate;

a front thru-bolt pivotally connecting said at least two front adjustment blocks to said front section of said frame;

a front adjustment connector connecting said at least two front adjustment blocks, said front adjustment connector having a threaded passage therethrough;

a front adjustment rod having a threaded end, said front adjustment rod passing through a hole in said front section of said frame and being connected to said front adjustment connector, said threaded end of said front adjustment rod engaging said threaded passage in said front adjustment connector; and, a front adjustment knob being fixed to said front adjustment rod.

17. The device according to claim 16 wherein said means for indicating said angle of said front plate comprise:

a front angle pointer being connected to said front thru-bolt, at least a portion of said front angle pointer extending alongside said front section of said frame; and, a front angle label being affixed to an outside surface of said front section of said frame, said front angle label comprising a relatively flat sheet of material having markings for indicating said angle of said front plate.

18. The device according to claim 17 wherein said markings indicate said angle of said front plate in degrees.

\* \* \* \* \*